United States Patent [19]

Meyer

[11] 4,058,833
[45] Nov. 15, 1977

[54] RADIATION IMAGING APPARATUS AND METHOD

[75] Inventor: Fred H. Meyer, Newbury, Ohio
[73] Assignee: Picker Corporation, Cleveland, Ohio
[21] Appl. No.: 537,776
[22] Filed: Dec. 31, 1974
[51] Int. Cl.² .............................................. H04N 5/32
[52] U.S. Cl. .................................... 358/111; 358/130
[58] Field of Search ...................... 178/6, 6.8, 7.2, 7.4, 178/6.7 A, DIG. 5, 7.85, 7.88; 358/111, 130, 131, 209, 225, 250

[56] References Cited

U.S. PATENT DOCUMENTS

| | | | |
|---|---|---|---|
| 3,118,971 | 1/1964 | Lovell | 178/7.4 |
| 3,337,685 | 8/1967 | Bougle | 178/7.88 |
| 3,439,114 | 4/1969 | Taylor | 178/6.8 |

*Primary Examiner*—Richard Murray
*Attorney, Agent, or Firm*—Watts, Hoffmann, Fisher & Heinke Co.

[57] ABSTRACT

An apparatus and method is disclosed for producing photographs and bright fluoroscopic television pictures of radiation patterns from a subject as converted to visible light images by an image tube. The apparatus includes a radiation source for directing X-radiation through a subject, and an image tube for receiving that radiation and producing in response thereto a visible image of the pattern of such radiation impinging upon the image tube. The apparatus also includes a film camera and a television camera for viewing the image tube output. A diverter apparatus controls the selective transmission of the light image from the image tube onto the film camera and television camera.

The film camera is directly aligned with the image tube output. The television camera is transversely displaced with respect to the image tube output. The diverter directs light from the image tube to the television camera in bursts syncronized with the field repetition rate of the television camera. During the remainder of the time, the diverter permits light from the image tube output to pass directly to the film camera.

34 Claims, 3 Drawing Figures

RADIATION IMAGING APPARATUS AND METHOD

CROSS-REFERENCE TO RELATED APPLICATIONS AND PATENTS

U.S. Pat. No. 3,173,008 issued Mar. 9, 1965, to D. M. Barrett, et al., entitled, SPOT FILMER.

U.S. Pat. Application, Ser. No. 537,730, concurrently filed, to Viktor Pleil, for X-RAY TUBE HAVING CATHODE BIAS CONTROL;

BACKGROUND OF THE INVENTION

1. Field of the Invention

This invention relates to apparatus and method for radiation imaging, and particularly to systems and methods for spot or cine photography and television imaging using a common image tube as an image source.

2. Description of the Prior Art

The utility of directing radiation, such as X-rays, through a subject and recording the pattern of this energy emerging from the subject is well known. In the field of medical diagnosis, for example, observation of the pattern of X-rays passing through the subject frequently yields valuable information as to the condition of the subject.

In certain medical applications, radiopaque material is injected into or ingested by the subject and X-rays are then directed through the subject. The accumulation or movement of such material in or about various portions of the body can be observed by noting the pattern of X-rays emerging from the body.

Two basic types of X-ray inspection include television imaging and film camera reproduction of a fluoroscopic image. Television imaging involves production of a continuous image of the region of interest, while film camera inspection is concerned with photographic exposures of an image of the radiation pattern from the subject, where high resolution is essential.

Television imaging is particularly useful in applications in which the areas of differing radiopacity in the subject exhibit motion or are otherwise time varying. Television, for example, can allow the physician to watch the progress of a radiopaque material ingested by the subject through the alimentary canal, or can be used to observe progress of such material injected into blood vessels.

An X-ray fluoroscopy system includes a X-ray source for directing X-rays through the subject, and an image tube located on the side of the subject opposite the X-ray source for converting the pattern of X-rays emerging from the subject to a visible light image. A television camera is positioned to view the image. Other television circuitry produces a display of that image.

A spot camera system includes an X-ray source for emitting X-rays of a relatively high intensity for a short time through the subject, and an image tube positioned as described above in the case of television. A camera having structure for supporting a roll of light sensitive film views the output of the image tube.

Systems have been constructed for combining television and spot camera capabilities, using only a single image tube. The advantages of such combinations of functions are that the examiner can operate continuously in the television mode to observe generally variations in the radiopacity of portions of the subject body, and can make and permanently record spot exposures of high resolution at specific desired times during these radiopacity variations.

Apparatus for performing combined television and spot exposures has typically included an X-ray tube for directing X-rays through the subject, an image tube opposite the source, a spot camera positioned at an angle displaced from the light image produced by the image tube, and a television camera aligned to directly view the light image at the image tube output.

A partially transmissive movable mirror, or beam splitter, is located in front of the image tube output, and acts as a divider of the image tube output image between the spot camera and the television camera. When only television is desired, the mirror is removed from the image tube output light path, allowing all the light from the tube to pass to the television camera. When spot exposures are desired, the mirror is swung into a second position across the image tube output light path, reflecting a portion of the light to the spot camera, from which spot exposures of the image at the at the output can be made.

Spot exposures require relatively high X-ray tube excitation to get a photographable light intensity at the image tube output, e.g., 600 milliamperes (m.a.) for 10–100 milliseconds. Television requires a substantially continuous X-ray output, but with an excitation of only about 7 m.a. or less.

This system has several disadvantages. It is desirable to reduce the time required to actuate the spot camera operation of such systems. It is also desirable to provide a simplified and improved diverter structure and method, for selectively directing the light output of the image tube to the spot camera and the television camera, which is relatively inexpensive, and trouble free.

In the prior systems, the partially transmissive mirror used for selectively dividing the image tube output image is mechanically swung between positions. This mechanical motion requires about one-half second to accomplish. A heavy and complex power source and linkage is required to swing the mirror in this amount of time, because the mirror itself has substantial inertia. Since the mechanical positioning of the mirror at its two positions is crucial in properly deflecting and transmitting the image, considerable adjustment of the mirror is necessary to keep it properly aligned. This tendency to misalignment is aggravated by the necessity for rapid movement of the mirror between positions.

Another factor which limits the speed at which the spot camera's function can be executed is that the X-ray tube requires time to vary its power output between the levels appropriate for television fluoroscopy and spot camera work.

The time lag involved in actuating the spot camera often required the taking of more spot photographs than are necessary. The time lag requires that the examiner anticipate accurately the occurrence of the event whose spot photography is desired. The patient was also often required to cooperate in ingesting radiopaque material in order to synchronize the movement of such material with the efforts of the examiner to photograph it. These techniques often involved a good deal of "cut and try" techniques in order to obtain the desired photographs. Additional required photographs subjected both the patient and the examiner to more radiation than is optimally possible, and also required more time, limiting the number of patients or subjects which can be examined with the system. In previous apparatus with television or optical viewing the exposure produced by the spot camera was undesirably affected because the image was degraded somewhat in the process of being reflected from, or transmitted through, the beam splitting mirror before it reached the spot camera. Any misalignment, mirror distortion or other system imperfections could only increase the image degratation.

In the prior system, the television picture often suffered from "flicker," resulting from undesired variations in light level input to the television camera. Such variations occurred when x-ray levels changed in the course of system operation.

The flickering could occur for several reasons. One cause of flicker was the pulsing of x-ray energy in synchronism with feed of film in the camera. If exposures were being taken at frame rates below about 45 frames a second, flickering of the TV image could not be avoided.

In most systems TV flicker is present whenever film is being exposed even if one does not pulse the x-ray tube. This is true because when energy levels are increased to produce sufficient light to expose the film, the television camera typically receives too much light and this results in a poor, if at all useful, image.

With a perfectly balanced system including an appropriate combination of film, beam splitter and TV camera, together with carefully controlled brightness on the output of the image tube, it is possible to achieve film exposure concurrently with a useful television image. While it is possible, even minute degradation or maladjustment in the system, or change in the film or the desired exposure level of the film, would result in an imbalance and a resultant degrading of the television image. In addition, while it is possible in a perfectly balanced system to achieve flicker-free television, the patient suffers more x-ray dosage than is required and accepted practice is to forego the advantage and pulse the x-ray energy in synchronism with the frame rate of the film camera to minimize dosage to the patient but with a resultant flickering TV image.

SUMMARY OF THE INVENTION

This invention includes a system and method for producing spot camera photographs and apparently continuous fluoroscopic images of a subject, derived from radiation from the subject.

An embodiment of the invention includes a radiation (preferably X-ray) source for directing radiation through the subject, and an image tube for receiving the radiation after passage through the subject, and converting the radiation to a visible light image at its output representing the pattern of received radiation. The apparatus further includes a spot camera for producing photographs of the visible image, and a television imaging system for producing a substantially continuous image of the radiation pattern from the subject.

The spot camera is a photographic camera with aperture and exposure control and means to support a portion of light-sensitive roll film for exposure to light entering the camera from the image tube output. Alternately, the spot camera can be replaced with a so-called "cine" camera for making motion pictures of the viewed image on light-sensitive film.

The television system includes a television camera positioned to view the image tube output, and associated television generating and control circuitry for producing an image from signals from the television camera. A display apparatus is provided to produce a bright visual image on a television screen of the image viewed by the television camera.

A diverter is also provided for the selective transmission of the output image from the image tube to the television camera and the spot camera.

To produce and maintain the continuous image, the television camera requires input of light from the image tube during only a portion of a plurality of predetermined time intervals. The spot camera requires a short duration, higher light intensity from the image tube than does the television camera, and has superior resolution capabilities.

One advantage of the inventive system is the minimization of the time during which the television camera must view the image tube output to maintain the continuous image. This is accomplished without sacrifice of television image quality, by synchronizing delivery of the light image to the television camera during only those periods when the field is being scanned.

The lag time for making spot camera photographs is also reduced. Since the time required for television viewing of the image is small, the remainder of the time during which the image output light can be directed to the spot camera is relatively great. This minimizes the time that the system must "wait" for spot photographs and enables the making of spot photographs at almost any time.

Another advantage is the reduction of distortion in the light energy directed to the spot camera and to the television camera.

The time duration of light energy required to operate the television camera is minimized by the structure of the diverter and the placement of the television and spot cameras. The diverter delivers the light to the television from the image tube output in bursts synchronous with and during the field generation time intervals of the television camera. The bursts each have a duration less than that of each time interval.

The diverter also, by way of a commutator, connected to the X-ray tube, pulses the X-ray output of the X-ray tube in synchronization with the deflection of the light energy to the television by the director.

In a form of the apparatus, the television camera is positioned transverse from the path of light from the image tube. The diverter includes a rotatable disc having a reflective portion and a light transmissive portion circumferentially displaced from each other, the disc being interposed in the light path from the image tube output. The diverter further includes a synchronous motor for rotating the disc to periodically interpose the reflective portion in the light path. The disc is positioned to reflect radiation to the television camera when the reflective portion is interposed in the path. The motor interposes the reflective portion in the path synchronously with the occurrence of the field scans of the television camera.

The high resolution of the spot camera is preferably enhanced by locating the spot camera at a position aligned with the light path from the image tube output. Radiation can thereby pass directly from the subject to the spot camera, eliminating intermediate reflection of the light and its resultant distortion.

A desirable feature of the system of this invention is the provision of an X-radiation source capable of very rapid variations in radiation output intensity. This flexibility accommodates the requirements of both the spot camera and the television fluoroscope. The rapid variability of such an X-radiation source enhances the operation of this system by taking full advantage of the provision of large time "windows" during which spot photographs may be taken, and reducing further the time lag previously attendant on making such spot photographs.

An object of this invention is to provide an improved method and system for producing continuous images and photographs of a subject from patterns of radiation from the subject.

Other features and objects of this invention will become apparent from the following drawings and detailed description.

DESCRIPTION OF THE PREFERRED EMBODIMENT

Figure 1:
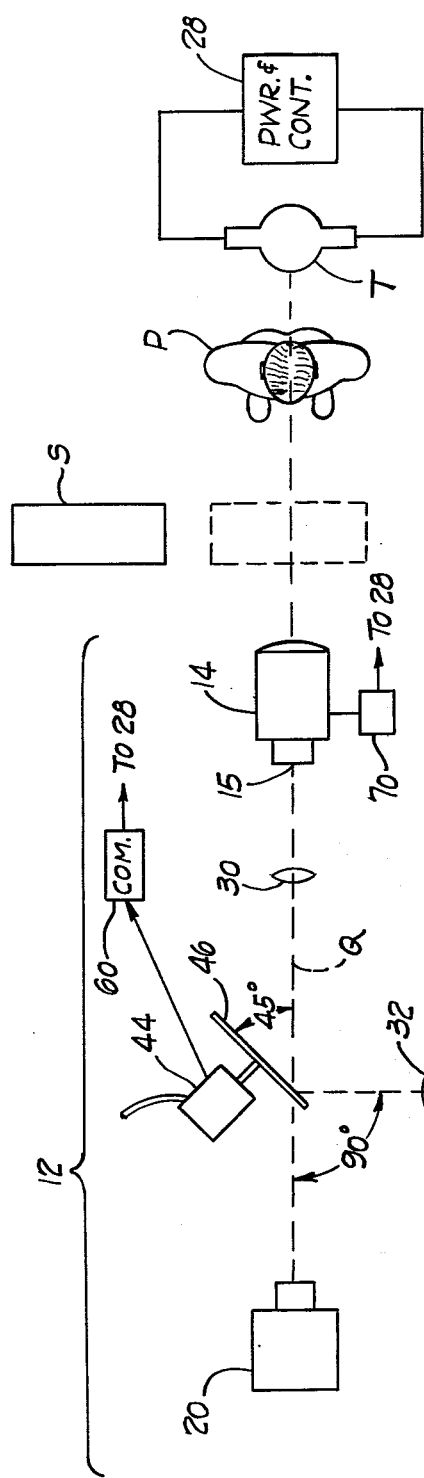
FIG. 1 is a top view, in diagrammatical form, of the system of this invention.

FIG. 1 shows an examination system for producing visual images of radiation emanating from a subject. The system includes a tube head T. The tube head T includes an X-ray tube which is a source of X-rays. X-rays are directed through a subject, shown in FIG. 1 as a patient P. The X-rays from the tube head T pass through the patient P and emerge from his body in patterns indicative of his condition.

The system 10 optionally includes a spot filmer S for making radiographic images of the patterns of radiation emerging from the body of the patient P, and a fluoroscopic system, generally designated as 12. The fluoroscopic system 12 responds to the radiation to produce light images representing the patterns of emerging radiation. The system 12 produces both spot or cine films representing the radiation patterns, and a continuous television display representing the energy patterns emerging from the body of the patient P.

The spot filmer S is movable into and out of interposition with the path of the X-ray patterns emerging from the body of the patient P. The spot filmer S is shown in solid line in FIG. 1 in its withdrawn position, and is shown in phantom in FIG. 1 in its operative position in the path of the X-rays. A suitable spot filmer is described in the referenced patent entitled, SPOT FILMER.

The fluoroscopic system 12 includes an image intensifier tube 14. The image intensifier tube 14 receives the X-radiation from the body of the patient P and converts this radiation to light images which appear at an output 15 of the image intensifier 14 and propagate along a path Q.

The fluoroscopic system 12 also preferably includes a television imaging system 16 for producing a video recording and the continuous display. The fluoroscopic system also includes camera 20 which may be either a spot or a cine camera. The camera 20 is positioned to receive light transmitted along the path Q.

A diverter 24 is interposed in the path Q of the light energy emanating from the output 15 of the image intensifier tube 14. The diverter 24 operates selectively to direct the light energy from the tube output 15 to the television imaging system 16 or to permit the direct transmission of light to the camera 20.

The camera 20 is preferably a spot camera having apparatus for supporting a portion of roll light-sensitive film in position to be exposed by light entering a lens assembly of the camera. The camera 20 has its lens assembly interposed in the path Q of the light energy from the image intensifier tube 14. Light from the image at the output 15 of the tube 14 thus passes directly to the lens of the camera 20 to expose its light-sensitive film. This arrangement eliminates distortion which might otherwise result if the light energy from the output 15 were reflected or otherwise processed before impingement upon the film in the spot camera 20.

Alternately the spot camera 14 can be replaced by a "cine" camera, i.e., a camera for making motion pictures of the image tube output image on light-sensitive film. A preferable camera is one made by Picker Corporation, Cleveland, Ohio, Ser. No. 3662.

A focusing lens 30 is positioned in the path Q between the output 15 of the image intensifier tube 14 and the diverter 24. The focusing lens 30 has its exit pupil located substantially downstream of the lens itself (to the left as shown in FIG. 1). Preferably, the exit pupil of the lens 30 should be located in the region of the diverter 24.

The television imaging system 16 is disposed transversely to the path Q. The television imaging system includes a focusing lens 32, a television camera 34, television generation and control circuitry 36, a television display or monitor 40, and a power supply 41.

The focusing lens 32 and the television camera 34 are preferably aligned perpendicularly with respect to the path Q, in the region of the diverter 24 as shown in FIG. 1.

The X-ray tube head T emits X-radiation through the body of the patient P for subsequent processing, as generally described above. The X-ray tube head T is preferably capable of emitting X-rays at any of three intensity levels. A first, or highest level, is used for making radiographs by use of the spot filmer S. In the system shown, a second, or intermediate level, is employed in making spot or cine films. A third, or still lower level, is employed for generating a continuous television image.

The X-ray tube T in the present system 10 is preferably constructed in accordance with the disclosure of a partial biased X-ray tube set forth in the concurrently filed application of Viktor W. Pleil, entitled, X-RAY TUBE HAVING CATHODE BIAS CONTROL U.S. Ser. No. 537,730. The X-ray tube disclosed therein has the particular facility for varying its intensity of X-ray output between the three levels with extreme rapidity. The applicability of this feature is discussed in more detail below.

The X-ray tube T is operated, and its intensity governed, by a means of power and control circuit 28 illustrated in FIG. 1. The power and control circuitry 28 is also shown and described in the referenced application of Pleil.

The television camera receives light energy from the output 15 of the tube 14 which is diverted by the diverter 24, and produces electrical video signals corresponding to the light energy it so receives. The television camera 34 is of known type. This camera is preferably a plumbicon, but is also suitably embodied by a vidicon or orthicon type, for example.

A television generation and control circuit 36 is well known as being suitable for operation on the video signals from the television camera 34 to cause generation of an image on a viewing screen. The television display 40 comprises a known type of television tube having a screen upon which the image viewed by the camera 34 is suitably caused to appear by the circuitry 36.

The diverter 24 includes a portion 42 of reflective material (see FIG. 2A) connected to a motive structure including an electric motor 44. The motor 44 functions to rotate the reflective portion 42 along a substantially circular path which causes the reflective portion to be alternately interposed in and removed from the path Q. When the reflective portion is removed from the path Q, the light from the tube output 15 is free to propagate directly to the spot camera 14. In this condition, none of the light from the path Q is reflected toward the television imaging system 16.

When the reflective portion is interposed in the path Q, the light energy emanating from the tube output 15 along the path Q is reflected through the focusing lens 32 and onto the input target screen of the television camera 34. Under this condition, the television imaging system 16 operates to produce a visual display on the television monitor 40 corresponding to the image produced at the tube output 15.

Preferably, the diverter 24 is positioned such that the reflective portion 42, when interposed in the path Q, is interposed at an angle of 45° (see FIG. 1). The television camera 34 is positioned perpendicular to the path Q, such that the light reflected by the reflective portion 42 is accurately directed to the television camera 34.

The diverter 24 also includes the power supply 41 which is connected to the motor 44 in order to drive that motor. Preferably, the power supply 41 also supplies power to the television imaging system 16.

The television camera 34 possesses a field repetition scan rate of 60 fields per second. The television camera 34 does not require the input of light continuously in order for it to generate its video signals. On the contrary, the television camera 34 requires only a short burst of light energy representing the image viewed during each field scanning cycle. Once this very short exposure of the television camera to the light energy is accomplished, the image lingers on the target of the television camera long enough for the camera to produce the video signals representing the viewed image, without the need for additional light energy during that frame.

It is an important feature of this invention that the motor 44 rotates the reflective portion 42 at a rate of speed which is synchronous with the field repetition scan rate of the television camera 34. Preferably, this rate of rotation is 60 revolutions per second, i.e., 3600 revolutions per minute.

The size of the reflective portion is preferably chosen such that the reflective portion 42 is interposed in the path Q for somewhat less than two milliseconds per revolution. Provided that the motor 44 rotates the reflective portion about its circular path in synchronism with the field repetition scanning of the television camera 34, the television camera receives a burst of light energy slightly less than 2 milliseconds in duration. This light energy is transmitted from and represents the image appearing at the output 15 of the image intensifier tube 14. This exposure of the television camera 34 to the image from the output 15 is sufficient to enable the television camera 34 and its associated imaging apparatus to generate a continuous and live display of the image produced by the tube 14.

Preferably, as stated above, the power supply 41 supplies power to both the television imaging system 16 and the motor 44. The motor 44 is of a synchronous type, and its connection to a common power source with the television camera 34 provides for its synchronization with the cyclical field repetition scan operation of the camera 34. If desired, the rotation of the motor 44 and the reflective portion 42 can also be phase locked with respect to the power supply from the power source 41.

Figure 2B:
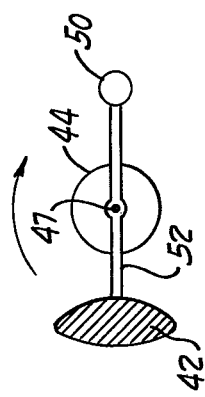
FIG. 2B is an elevational view showing an alternate form of the portion of the system of FIG. 1 shown in FIG. 2A.
Figure 2A:
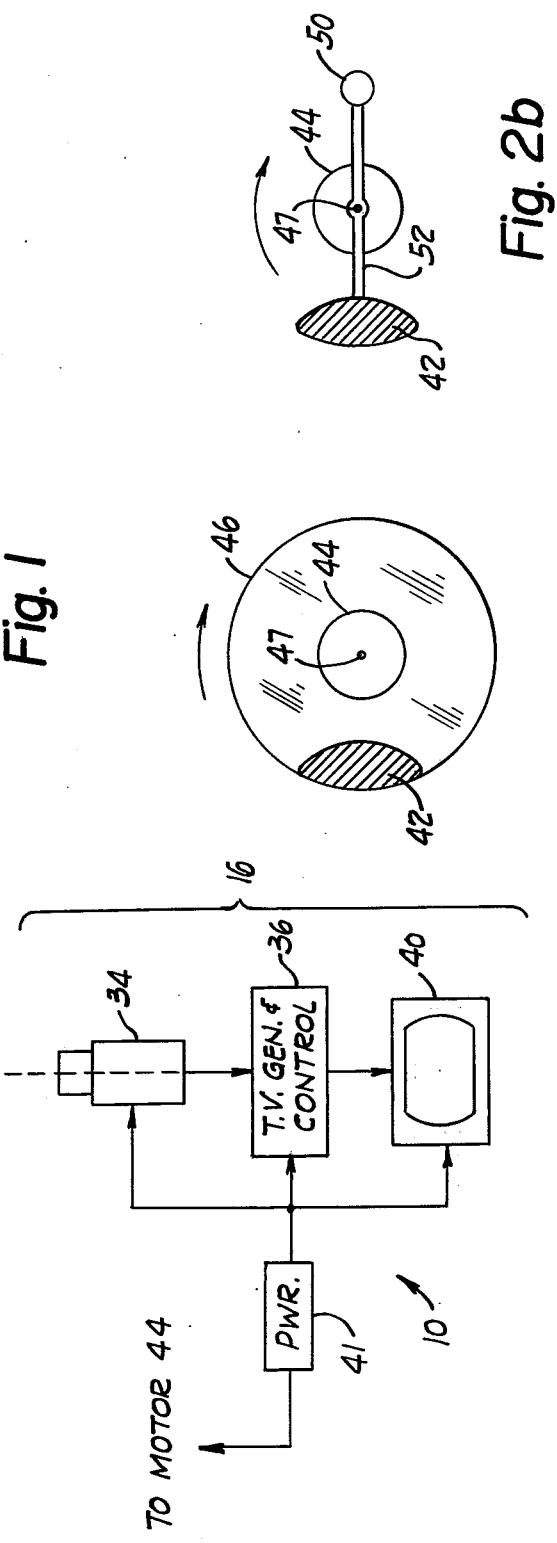
FIG. 2A is an elevational view showing a first form of a portion of the system shown in FIG. 1.

Referring to FIG. 2A, the reflective portion 42 is shown as mounted on a portion of a rotatable disc 46. The disc is made of glass, approximately third-eighth inch in thickness. The disc is mounted at 47 on the drive shaft of the motor 44 for clockwise rotation as viewed in FIG. 2A and indicated by the arrow. The portion of the disc 46 which lies outside the reflective portion 42 is transparent. This permits the passage of light from the tube output 15 to the spot camera 20 whenever the reflective portion 42 of the disc 46 is not interposed in the path Q.

The reflective portion 42 shown in FIG. 2A is a coating of silver material applied to the side of the disc 46 which generally faces the tube output 15.

FIG. 2B shows another embodiment of the reflective portion 42 and its means of mounting on the drive shaft of the motor 44. In this instance, the reflective portion is connected to the drive shaft 47 of the motor 44 and to a counterweight 50 by way of a connecting element 52.

In operation, the structure as illustrated in FIG. 2B is rotated in the direction shown by the arrow by the motor 44 in synchronism with the field repetition rate of the television camera 34, as in the case of the arrangement shown in FIG. 2A.

The advantage of the construction of FIG. 2B is that the glass portion of the disc 46 is eliminated. This enables the light energy from the tube output 22 to pass directly to the spot camera 20 without any optical impedance whatever. This further reduces the likelihood of distortion of the light energy reaching the spot camera 20, by eliminating whatever effects the transparent portion of the glass of the disc 46 may have upon the light energy passing through it.

The significance of the operation of the diverter 24, and its relationship with the spot camera 20 and the television imaging system 16, can best be understood with an explanation of the operation of the system.

In operation, the patient P is placed between the output of the X-ray tube T and the image intensifier tube 14. When only a television fluoroscopic image of the radiation patterns from the patient is desired, the X-ray tube T is actuated to emit X-rays at its lowest intensity level, as described above. In this mode, a pulsed current is applied to the X-ray tube, by means of a commutator 60 connected to the motor 44 and the tube control circuitry 28. The current, and the X-rays from the tube, are pulsed in synchronism with the interposition of the reflective surface 42 in the path Q. The duration of the X-ray pulses is controlled by a brightners stabilizer 70, which senses the light energy at the tube output 15, and controls the pulse duration for constant exposure. This stabilization system is also employed in making spot photographs. The image intensifier tube 14 receives the X-rays passing through the patient from the tube T and generates a light image at its output 15 which propagates along the path Q. The motor 44 is operated to rotate the disc 46 and the reflective portion 42 at a rate of speed such that the reflective portion 42 passes through the path Q at intervals which are synchronous with the field repetition scan rate of the television camera 34. As explained above, under these conditions, bursts of light energy representing the image appearing at the output 15 are transmitted in approximately 2 millisecond pulses to the television camera 34 in synchronism with its field repetition rate. This amount of light energy is sufficient to enable the television imaging system 16 to produce useful television images of the image at the output 15.

When it is desired to make a spot camera exposure of the image at the output 15, the X-ray tube T is actuated to produce X-rays at its middle level of intensity. This middle level actuation has a duration of approximately 10–50 milliseconds, and involves the passage of approximately 600 milliamperes of current through the X-ray tube. This actuation is governed to take place only during the time in which the reflective portion 42 is removed from the path Q. This allows the higher intensity light energy necessary for spot camera operation to propagate along the path Q to the spot camera 20. Conversely, none of the light energy generated by the higher intensity level of X-rays is deflected toward the television camera 34. This feature overcomes the disadvantage of the prior art wherein Rather, the television imaging system 16 is not affected by higher level burst of energy utilized in making the photographs with the camera 20.

The high speed of rotation of the diverter 24 enables the substantially instantaneous taking of still photographs with the spot camera 20, through the time "windows" provided by the recurrent periods (about 17 milliseconds) during which all the light is passed directly to the spot camera 20. This eliminates the time lag necessary for taking spot photographs which was inherent in the prior art, and made necessary by the time required to pivot a heavy partially transmissive mirror from one position to another before being able to take the spot photograph.

If the spot exposure is longer than 17 milliseconds, the X-ray tube T is controlled to switch to its middle level during a number of successive time "windows" when the reflective portion 42 is not in the path Q.

The invention has been shown in connection with a preferred embodiment, but it will be readily apparent to those skilled in the art that various changes in the form and arrangement of parts may be made to suit requirements without departing from the spirit and scope of this invention as defined by the appended claims.

What is claimed is:

1. A system for deriving diagnostic information about a subject from a pattern of penetrative radiation, said system comprising:
   a. a source of directing penetrative radiation at different energy levels along a path through the subject;
   b. an image tube for receiving penetrative radiation from the subject and converting such radiation to an output light image representing a pattern of such radiation from said subject;
   c. a film camera for receiving said light image for producing photographs thereof;
   d. a television apparatus for producing a substantially continuous image of said light image from light received by said television apparatus during each of a plurality of predetermined time intervals; and,
   e. a diverter for controlling the selective transmission of light energy from said output image to said film camera and to said television apparatus to direct only said light to said television apparatus in bursts having a predetermined energy and substantially synchronously with the occurrence of said predetermined time intervals, for limiting the time duration and energy intensity of light energy transmission to the television apparatus to maintain said continuous television image at a substantially constant brightness, and to maximize the time during which said light energy can be utilized with said film camera for producing photographs while still producing the continuous television image.

2. The system of claim 1, wherein said diverter comprises:
   a. a portion of radiation reflective material, and,
   b. motive structure connected to said reflective portion for moving said reflective portion between a first position in which said light energy is directed toward one of said television apparatus and camera and a second position in which said light energy is directed to the other of said television apparatus and said camera.

3. The system of claim 2, wherein said diverter further comprises:
   structure for mounting said reflective portion for rotative movement along a substantially circular path, said reflective portion assuming said first position during its traversal of a portion of said circular path.

4. The system of claim 3, wherein:
   a. said rotative mounting structure and said reflective portion comprise a substantially circular rotatable disc, said reflective portion being disposed on a portion of said disc, said disc further having a light transmissive portion; and,
   b. said motive structure is connected to said disc and comprises a synchronous motor for rotating said disc.

5. The system of claim 4, wherein:
   a. said television apparatus includes a television camera operable at a field repetition rate of substantially X fields per second, said time intervals being coincident with said field repetition rate; and,
   b. said motive structure is arranged to rotate said disc at substantially X revolutions per second to effect said disposition of said reflective portion in said first position synchronously with said occurrence of said field repetitions.

6. The system of claim 1, wherein:
   a. said film camera is aligned with the path of light energy from said output image;
   b. said television camera is disposed at a location transverse to said light energy path; and,
   c. said light energy propagates directly to said film camera along said path when said diverter does not direct said radiation to said television camera.

7. The system of claim 1, wherein:
   a. said source is controllable to produce radiation at a first higher intensity and a second lower intensity; and,
   b. said system further comprises control circuitry connected to said source for causing said source to produce radiation at said lower intensity during the time when light energy is transmitted to said television apparatus and at said higher intensity during another time.

8. The system of claim 1, further comprising:
   a focusing lens interposed between said diverter and said television apparatus for focusing light energy directed toward said television apparatus by said diverter.

9. The system of claim 1, wherein said bursts have a duration of approximately 2 milliseconds.

10. A method for producing diagnostic information about a subject from a pattern of penetrative radiation passing through the subject utilizing a system including a film camera for producing photographs of the subject and a television apparatus for producing a substantially continuous image of the subject in response to receipt of energy during a plurality of predetermined time intervals, said method comprising the steps of:
   a. directing penetrative radiation through the subject;
   b. subsequently producing and directing an energy representation of the patterns of such penetrative radiation to said film camera, and to said television apparatus in discrete quantities occurring substantially synchronously with the occurrence of each of said plurality of predetermined time intervals, for limiting the duration of energy transmission to said television apparatus to enable production and maintenance of said continuous image, while optimizing the time during which such energy can be directed to the film camera for producing photographs.

11. The method of claim 10, wherein said energy directing step comprises:
   a. moving a portion of reflective material between a first position to reflect said radiation toward said television apparatus and at least a second position; and,
   b. transmitting said energy representation toward said film camera when said reflective portion is disposed in said second position.

12. The method of claim 11, wherein said moving step comprises rotating said reflective portion in a substantially circular path, said reflective portion assuming said first position during its traversal of a portion of said circular path.

13. The method of claim 12, in which said television apparatus operates at a predetermined field repetition rate, said moving step further comprising:
   moving said reflective portion in said substantially circular path at a frequency of revolution substantially equal to the frequency of said field repetition rate to effect said disposition of said reflective portion in said first position synchronously with the occurrence of each field of said television fluoroscope.

14. The method of claim 10, in which the film camera is aligned to directly receive said energy representation along an energy path, and the television camera is disposed transversely with respect to said energy path, and wherein:
   a. said directing step comprises reflecting said energy from said path to one of said cameras; and,
   b. said method further comprises the step of passing said energy directly along said path to the other of said cameras when said radiation is not reflected to said first camera.

15. The method of claim 14 wherein the television camera is said one camera.

16. The method of claim 10, further comprising the steps of:
   a. producing penetrative radiation at a first lower intensity while said energy representation is directed to said television camera; and,
   b. producing said penetrative radiation at a second higher intensity at another time.

17. A method for producing a visual image of a subject from patterns of penetrative radiation transmitted along a path from the subject, utilizing a system including means for causing the emanation of penetrative radiation from the subject and a television apparatus comprising a television camera responsive to said radiation for generating video signals representative of said penetrative radiation at a predetermined rate of field repetition, said method comprising the steps of:
   a. passing penetrative radiation through a subject to produce radiation patterns along the path; and,
   b. diverting energy representing said radiation patterns from the subject to said television camera substantially synchronously with the occurrence of each of said field repetitions, during a portion of the time required for generation of each field repetition, and at an energy intensity controlled to limit the amount and time duration of energy incident on the camera for enabling the television apparatus to produce and maintain substantially flicker free and continuous images representative of the radiation patterns from the subject.

18. A system for producing visual images of energy representations of patterns of radiation from a subject, said system comprising:
   a. means for directing said energy representations along a path;
   b. a first camera aligned with said path for producing photographs of said energy representations incident on said first camera;
   c. a television apparatus transversely displaced from said path for producing substantially continuous images of energy received by said television apparatus;
   d. a diverter for directing only a portion of said energy representations from said path to said television apparatus, and other portions of said energy representations not so directed propagating along said path to said first camera, enabling said first camera to receive undiverted energy representations which are thereby not susceptible to distortion in said diversion.

19. A system for producing visual images of a subject from patterns of radiation from the subject, said system comprising:
   a. a first recording apparatus for producing and recording representations of said patterns incident thereon;
   b. a television apparatus including a television camera responsive during predetermined time intervals to said patterns to maintain a continuous image representing said patterns, said intervals corresponding to the field repetition scan rate for said television camera; and,
   c. transmission means for enabling said television to respond to said radiation patterns in synchronism with the field scan repetition rate of said television camera.

20. The system of claim 19, wherein said transmission means comprises:
   reflective structure for exposing said television camera to the influence of said radiation patterns during only predetermined time intervals.

21. A system for deriving visual images of a subject from patterns of radiation passing through the subject, said system comprising:

a. a television apparatus including a television camera responsive to said patterns of radiation for generating video signals representing said radiation patterns at a predetermined rate of field scanning repetition; and, b. apparatus for causing said television apparatus to respond to said radiation patterns during only predetermined time intervals, said time intervals occurring substantially in synchronism with the occurrence of each said field repetition, for minimizing the amount of radiation required to enable the television camera to produce and maintain a substantially constant image representative of the patterns of radiation from the subject.

22. The system of claim 21, further comprising:
a film camera responsive to said patterns of radiation for making photographs thereof.

23. The system of claim 22, further comprising:
a. means for converting said patterns of radiation to energy representations of said patterns and directing said energy representations along a path;
b. said film camera being substantially aligned with said path to receive said energy representations directly;
c. said television camera being transversely displaced with respect to said path; and,
d. said response causing apparatus comprising structure for directing said energy representations to said television camera in discrete quantities occurring only during said predetermined time intervals.

24. A diverter for use in a system for producing visual images of a subject in response to patterns of radiation from the subject, the system including means for propagating representations of said radiation along a path, a first image producing apparatus, and a second image producing apparatus including a television camera having a predetermined rate of field scan repetition, said diverter comprising:
structure for directing said radiation representations to said television camera in discrete quantities, said direction of such quantities being synchronous with the field scan repetition rate of said camera, and said structure causing said representations to be incident on said first recording apparatus at other times.

25. The diverter of claim 24, further comprising:
a. a portion of material capable of reflecting said representations; and,
b. motive structure connected to said reflective portion for moving said reflective portion synchronously with the occurrence of said field scan repetitions of said television camera; and,
c. said movement being between a first position to reflect said representations toward said television camera, and a second position.

26. The diverter of claim 25, further comprising:
structure for mounting said reflective portion for rotative movement along a substantially circular path, said reflective portion assuming said first position during its traversal of a portion of said circular path.

27. The diverter of claim 26, wherein:
a. said rotative mounting structure and said reflective portion comprise a substantially circular disc, said reflective portion being disclosed on a portion of said disc, said disc further having a light transmissive portion; and,
b. said motive structure being connected to said disc for axial rotation of said disc, and comprising a synchronous electric motor for rotating said disc at a predetermined speed.

28. The diverter of claim 27, wherein:
said synchronous electric motor is an hysteresis motor.

29. The diverter of claim 25, wherein said reflective portion is made of polished beryllium.

30. The diverter of claim 29, wherein:
said rotative mounting structure comprises a counterweight, and a connective element extending between said counterweight and said reflective portion, said connecting element being rotatably mountable at the combined center of mass of said counterweight, connective element and reflective portion, for balanced rotation of said reflective portion along a circular path.

31. A system for producing diagnostic information about a subject comprising:
a. a source for directing penetrative radiation through the subject and emerging in a pattern along a path beyond the subject;
b. apparatus for converting the radiation pattern to a corresponding light image;
c. a film camera positioned to receive the light image without substantial degradation;
d. optical apparatus transverse from the path for viewing the light image when said image is directed to the optical apparatus, and
e. apparatus for intermittently directing sufficient light from the light image to the optical apparatus for producing an apparently flicker-free image while directing most of the light to the film camera to facilitate its use in making photogaphs at randomly selected times.

32. An X-ray diagnostic system comprising:
a. an x-ray source for pulsing between first and second energy levels;
b. an image device positioned to receive x-rays from the source and to produce a shadow image of a subject between the source and the device;
c. first and second imaging assemblies for selective operation when the source is operated at the first and second energy levels respectively,;
d. a movable reflector;
e. reflector drive means for moving the reflector in coordination with the source pulsing to reflect an image to the first assembly at times when the source is at its first energy level; and
f. the second assembly being positioned to receive an image at times when the source is at its second energy level.

33. The system of claim 32, wherein:
the reflector is a mirror mounted for orbital movement for intercepting the image once during each orbit.

34. A system for producing medical diagnostic information about a subject, comprising:
a. a source for directing radiation through the subject;
b. apparatus for producing a visible light image of the radiation emerging from the subject;
c. a film camera;
d. an optical apparatus for viewing the visible light image, and
e. a diverter for directing energy from the visible light image exclusively toward one of the camera and the optical apparatus at a time in accordance with a predetermined sequence for minimizing the required radiation intensity and image brightness for operating each of the camera and optical apparatus.

* * * * *

UNITED STATES PATENT AND TRADEMARK OFFICE
CERTIFICATE OF CORRECTION

PATENT NO. : 4,058,833
DATED : November 15, 1977
INVENTOR(S) : Fred H. Meyer

It is certified that error appears in the above–identified patent and that said Letters Patent are hereby corrected as shown below:

Column 2, line 20, delete "at the", first occurrence.

Column 3, line 6, "degratation" should be --degradation--.

Column 5, line 55, after "intensifier" insert --tube--.

Column 8, line 13, "third-eighth" should be --three-eighth--;
line 60, "brightners" should be --brightness--.

Column 9, line 25, after "wherein" insert --the television image tended to flicker when cine or spot camera pictures were taken.--.

Column 13, line 64, "disclosed" should be --disposed--.

Column 14, line 41, after "respectively" delete -- , --.

Signed and Sealed this

Sixteenth Day of May 1978

[SEAL]

Attest:

RUTH C. MASON
Attesting Officer

LUTRELLE F. PARKER
Acting Commissioner of Patents and Trademarks